(12) United States Patent
Sulakvelidze et al.

(10) Patent No.: US 7,674,467 B2
(45) Date of Patent: Mar. 9, 2010

(54) SALMONELLA BACTERIOPHAGE AND USES THEREOF

(75) Inventors: Alexander Sulakvelidze, Towson, MD (US); Shanmuga Sozhamamnnan, Timonium, MD (US); Gary R. Pasternack, Baltimore, MD (US)

(73) Assignee: Intralytix, Inc., Baltimore, MD (US)

( * ) Notice: Subject to any disclaimer, the term of this patent is extended or adjusted under 35 U.S.C. 154(b) by 0 days.

(21) Appl. No.: 11/661,689

(22) PCT Filed: Sep. 3, 2004

(86) PCT No.: PCT/US2004/028634

§ 371 (c)(1),
(2), (4) Date: Dec. 14, 2007

(87) PCT Pub. No.: WO2005/024005

PCT Pub. Date: Mar. 17, 2005

(65) Prior Publication Data

US 2008/0118468 A1    May 22, 2008

Related U.S. Application Data

(60) Provisional application No. 60/499,339, filed on Sep. 3, 2003.

(51) Int. Cl.
  *A61K 39/12* (2006.01)
(52) U.S. Cl. .............................. 424/204.1; 424/258.1
(58) Field of Classification Search .................. None
  See application file for complete search history.

(56) References Cited

U.S. PATENT DOCUMENTS 2,851,006 A * 9/1958 Taylor et al. .............. 119/6.8
6,699,701 B1 * 3/2004 Sulakvelidze et al. ..... 435/235.1

* cited by examiner

*Primary Examiner*—Stacy B Chen
(74) *Attorney, Agent, or Firm*—Hunton & Williams LLP

(57) ABSTRACT

The present invention is directed to isolated *Salmonella* bacteriophage, and methods of using *Salmonella* bacteriophage, or polynucleotides and polypeptides derived therefrom, to control the growth or contamination of food products by *Salmonella*. The present invention also contemplates the use of *Salmonella* bacteriophage, and polynucleotides and polypeptides derived therefrom, for the treatment of host infections or environmental contamination by *Salmonella*.

8 Claims, 8 Drawing Sheets

Figure 1A- Electron Micrographs of *Salmonella* bacteriophage SPT-1
Table of approximate size:
| Phage | Size | |
|---|---|---|
| | Head (nm) | Tail (nm) |
| SPT-1 | 78 x 70 | 122 x 22 |
original EM's were 297,000 X.
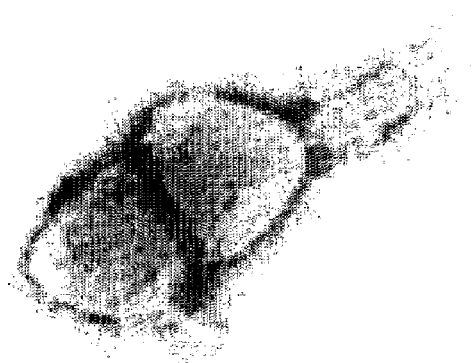

Figure 1B- Electron Micrographs of *Salmonella* bacteriophage SBA-178
Table of sizes:
| Phage | Size | |
|---|---|---|
| | Head (nm) | Tail (nm) |
| SBA-178 | 70 x 68 | 117 x 17 |
original EM's were 297,000 X.
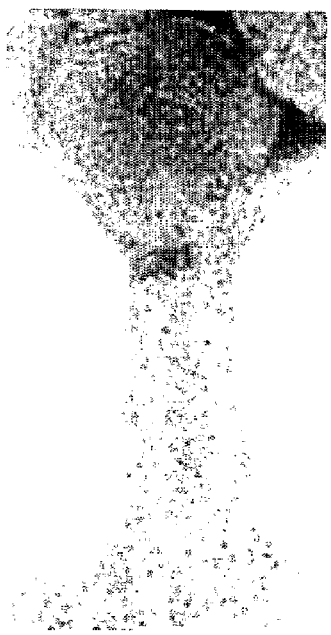

Figure 1C- Electron Micrographs of *Salmonella* bacteriophage SBA-1781
Table of sizes:
| Phage | Size | |
|---|---|---|
| | Head (nm) | Tail (nm) |
| SBA-1781 | 76 x 71 | 101 x 22 |
original EM's were 297,000 X.
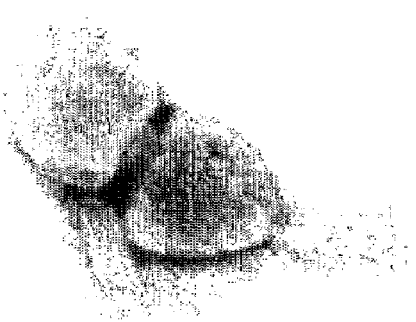

Figure 1D- Electron Micrographs of *Salmonella* bacteriophage SIT-128
Table of sizes:
| Phage | Size | |
|---|---|---|
| | Head (nm) | Tail (nm) |
| SIT-128 | 69 x 70 | 110 x 15 |
original EM's were 297,000 X.

Figure 1E- Electron Micrographs of *Salmonella* bacteriophage SSE-121
Table of sizes:
| Phage | Size | |
|---|---|---|
| | Head (nm) | Tail (nm) |
| SSE-121 | 79 x 82 | 117 x 13 |
original EM's were 297,000 X.

Figure 1F- Electron Micrographs of *Salmonella* bacteriophage SDT-15
Table of sizes:
| Phage | Size | |
|---|---|---|
| | Head (nm) | Tail (nm) |
| SDT-15 | 69 x 67 | 102 x 20 |
original EM's were 297,000 X.

Figure 2A- PFGE Profile for *Salmonella* bacteriophage

Figure 2B- RFLP Profile for *Salmonella* bacteriophage

Figure 2A-PFGE

Low-range PFGE marker:
New England Biolabs, Inc

Figure 2B-RFLP

1 Kb marker: MBI-
Fermentas: GeneRuler™
DNA Ladder Mix

**Figure 3- SDS-PAGE Protein Profile for *Salmonella* bacteriophage**
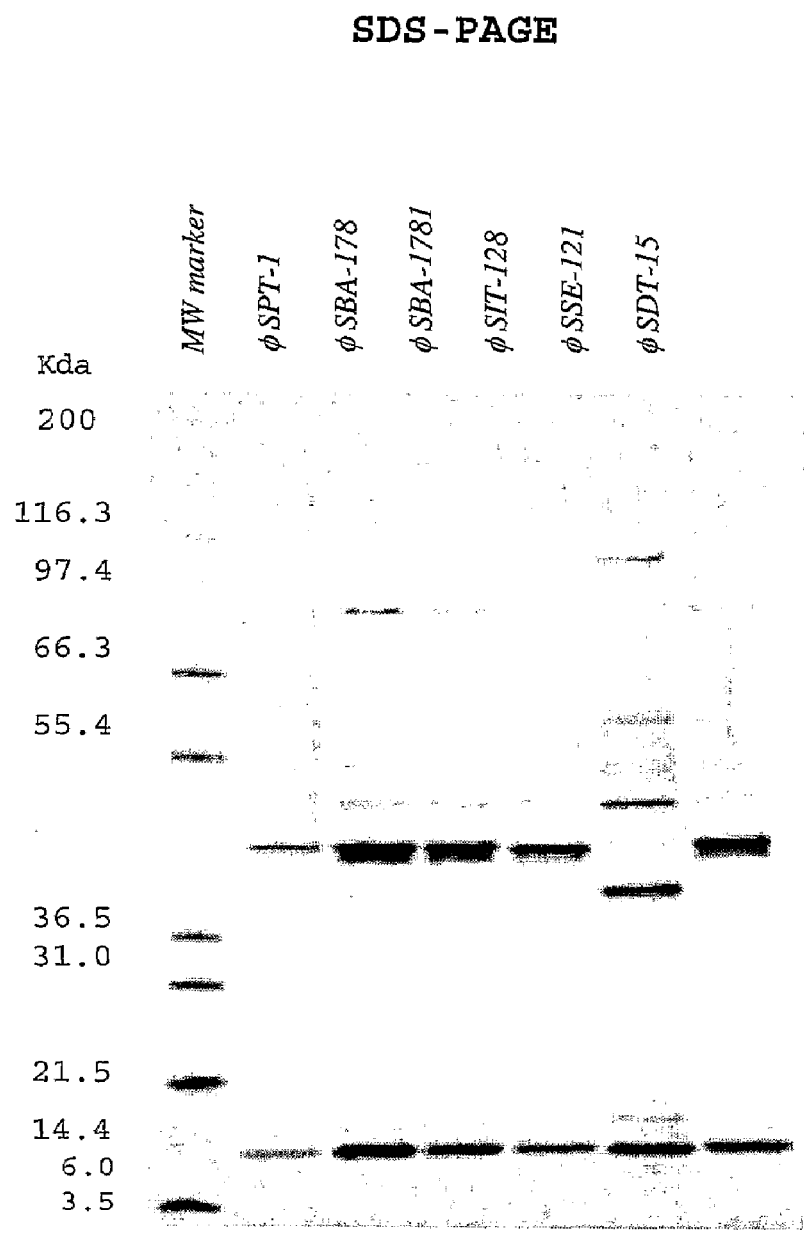

SALMONELLA BACTERIOPHAGE AND USES THEREOF

This application is a National Phase filing of International Application No. PCT/US2004/028634, filed Sep. 3, 2004, which claims priority to U.S. Provisional Patent Application No. 60/499,339, filed Sep. 3, 2003.

FIELD OF THE INVENTION

The present invention relates to novel bacteriophage, and compositions corresponding thereto. More specifically, isolated *Salmonella* bacteriophage compositions are provided having lytic specificity for *Salmonella*, and are useful for controlling growth of *Salmonella*, as well as the infection or colonization of food products or food processing equipment by *Salmonella*, to control the infection or colonization of processed and unprocessed food products by *Salmonella*, or to control the colonization of equipment involved in the processing of the same food product(s). The invention also provides methods of detecting the presence of *Salmonella* cells on processed or unprocessed food products, or equipment involved in the processing of the same food products. The invention additionally provides methods of using *Salmonella* bacteriophage for the removal of antibiotic-resistant or other undesirable pathogens from medical, veterinary, animal husbandry, and other environments where they may be passed to humans or animals. The invention additionally provides for methods of using *Salmonella* bacteriophage to treat human (animal) diseases caused by *Salmonella*. The invention also relates to methods of producing *Salmonella* bacteriophage and corresponding polynucleotides and polypeptides.

BACKGROUND OF THE INVENTION

There are six major families of bacteriophages including Myoviridae (T-even bacteriophages), Styloviridae (Lambda bacteriophage groups), Podoviridae (T-7 and related bacteriophage), Microviridae (X174 group), Leviviridae (for example, *E. coli* bacteriophage MS2) and Inoviridae as well as coliphages, in general. Other bacteriophage families include members of the Cystoviridae, Microviridae, and Siphoviridae families.

Bacteriophage has been used therapeutically for much of this century. Bacteriophage, which derive their name from the Greek word "phago" meaning "to eat" or "bacteria eaters", were independently discovered by Twort as well as by D'Herelle in the first part of the twentieth century. Early enthusiasm led to the use of bacteriophage as both prophylaxis and therapy for diseases caused by bacteria. However, the results from early studies to evaluate bacteriophage as antimicrobial agents were variable due to the uncontrolled study design and the inability to standardize reagents. Later, in better designed and controlled studies, it was concluded that bacteriophage were not useful as antimicrobial agents (Pyle, N. J., *J. Bacteriol*, 12:245-61 (1936); Colvin, M. G., *J. Infect. Dis.*, 51:17-29 (1932); Boyd et al., Trans R. Soc. Trop. Med. Hyg., 37:243-62 (1944)).

This initial failure of phage as antibacterial agents may have been due to the failure to select for phage that demonstrated high in vitro lytic activity prior to in vivo use. For example the phage employed may have had little or no activity against the target pathogen, or they may have been used against bacteria that were resistant due to lysogenization or the phage itself may have been lysogenic for the target bacterium (Barrow, et al., "Bacteriophage therapy and prophylaxis: rediscovery and renewed assessment of potential" *Trends in Microbiology,* 5:268-71 (1997)). However, with better understanding of the phage-bacterium interaction and of bacterial virulence factors, it has been possible to conduct studies which demonstrated the in vivo anti-bacterial activity of the bacteriophage (Asheshov, et al., *Lancet*, 1:319-20 (1937); Ward, W. E., *J. Infect. Dis.,* 72:172-6 (1943); Lowbury, et al., *J. Gen. Microbiol.,* 9:524-35 (1953)). In the U.S. during the 1940's the Eli Lilly Co. commercially manufactured six phage products for human use, including preparations targeted towards *Staphylococci, Streptococci* and other respiratory pathogens.

With the advent of antibiotics, the therapeutic use of phage gradually fell out of favor in the U.S. and Western Europe, and little subsequent research was conducted. However, in the 1970's and 1980's bacteriophage therapy continued to be utilized in Eastern Europe, most notably in Poland and the former Soviet Union. Alisky et al. conducted a review of all Medline citations where bacteriophage was employed therapeutically from 1966 to 1996 (Alisky et al, "Bacteriophages show promise as antimicrobial agents." *J. Infect.,* 36-5-15 (1998)). There were twenty-seven papers from Britain, the U.S.A., Poland and the Soviet Union.

There are also several British studies describing controlled trials of bacteriophage raised against specific pathogens in experimentally infected animal models such as mice and guinea pigs (See, e.g., Smith, H. W., and M. B. Huggins "Successful treatment of experimental *Escherichia coli* infections in mice using phages: its general superiority over antibiotics" *J. Gen. Microbiol.* 128:307-318 (1982); Smith, H. W., and M. B. Huggins "Effectiveness of phages in treating experimental *E. coli* diarrhea in calves, piglets and lambs" *J. Gen. Microbiol,* 129:2659-2675 (1983); Smith, H. W. and R. B. Huggins "The control of experimental *E. coli* diarrhea in calves by means of bacteriophage" *J. Gen. Microbiol.,* 133: 1111-1126 (1987); Smith, H. W., R. B. Huggins and K. M. Shaw "Factors influencing the survival and multiplication of bacteriophages in calves and in their environment" *J. Gen. Microbiol.,* 133:1127-1135 (1987)). These trials measured objective criteria such as survival rates. Efficacy against *Staphylococcus, Pseudomonas* and *Acinetobacter* infections were observed. These studies are described in more detail below.

One such study concentrated on improving bioavailability of phage in live animals by modifying the bacteriophage (Merril, C. R., et al., "Long-circulating bacteriophage as antibacterial agents" *Proc. Natl. Acad. Sci.* USA, 93:3188-3192 (1996)). Reports from the U.S. relating to bacteriophage administration for diagnostic purposes have indicated phage have been safely administered to humans in order to monitor humoral immune response in adenosine deaminase deficient patients (Ochs, et al., "Antibody responses to bacteriophage (Φ174 in patients with adenosine deaminase deficiency" *Blood,* 80:1163-71 (1992)) and for analyzing the importance of cell-associated molecules in modulating the immune response in humans (Ochs, et al., "Regulation of antibody responses: the role of complement and adhesion molecules." *Clin. Immunol. Immunopathol.,* 67:S33-40 (1993)).

Additionally, Polish, Georgian, and Russian papers describe experiments where phage was administered systemically, topically or orally to treat a wide variety of antimicrobial resistant pathogens (See, e.g., Shabalova, I. A., et al., "*Pseudomonas aeruginosa* bacteriophage in treatment of *P. aeruginosa* infection in cystic fibrosis patients," Abstr. 443. In Proceedings of IX International Cystic Fibrosis Congress, Dublin, Ireland; Slopek, S., et al., "Results of bacteriophage treatment of suppurative bacterial infections I. General evaluation of the results." *Archivum. Immunol. Therapiae Experi-* mental, 31:267-291 (1983); Slopek, S., et al., "Results of bacteriophage treatment of suppurative bacterial infections in the years 1981-1986" *Archivum Immunol. Therapiae Experimental*, 35:569-83 (1987)).

Infections treated with bacteriophage included osteomyelitis, sepsis, empyema, gastroenteritis, suppurative wound infection, pneumonia and dermatitis. Pathogens treated with the bacteriophage include *Staphylococci, Streptococci, Klebsiella, Shigella, Salmonella, Pseudomonas, Proteus* and *Escherichia*. Articles have reported a range of success rates for phage therapy between 80-95% with only rare reversible allergic or gastrointestinal side effects. These results indicate that bacteriophage may be a useful adjunct in the fight against bacterial diseases.

Despite the use of bacteriophage for the treatment of diseases in humans, there remains in the art a need for the discovery of novel bacteriophage and methods for using these bacteriophage in several critical areas. One significant need concerns the treatment of processed or unprocessed food products to treat or prevent colonization with undesirable *Salmonella* such as pathogens responsible for foodborne illness and food spoilage organisms. A second critical area of need concerns the removal of undesirable bacteria from industrial environments such as food processing facilities to prevent colonization thereof. A third critical area of need concerns the removal of antibiotic resistant organisms from environments where they may be passed to susceptible humans and animals, such as hospitals, nursing homes, veterinary facilities, and other such environments. Finally, new bacteriophage and methods of using the same are needed for the treatment of human bacterial disease, particularly those diseases caused by antibiotic-resistant organisms.

SUMMARY OF THE INVENTION

The invention meets those needs and more by providing compositions comprising novel *Salmonella* bacteriophage having lytic specificity for *Salmonella*. The invention additionally provides methods of using *Salmonella* bacteriophage, to control or prevent the infection or colonization of processed and unprocessed food products by *Salmonella*, or colonization of equipment involved in the processing of the same food product(s). The invention also provides methods of detecting the presence of *Salmonella* cells on processed or unprocessed food products, or equipment involved in the processing of the same food products. The invention additionally provides methods of using *Salmonella* bacteriophage for the removal of antibiotic-resistant or other undesirable pathogens from medical, veterinary, animal husbandry, and other environments where they may be passed to humans or animals. The invention additionally provides for methods of using *Salmonella* bacteriophage to treat human and/or other animal diseases caused by *Salmonella*.

BRIEF DESCRIPTION OF THE FIGURES

Figures

FIGS. 1A-F- FIGS. 1A-F are electron microscope images of *Salmonella* bacteriophage performed at 297,000× essentially as described in Carlson, K., "Visualization of T4 phage by electron microscopy", in *Molecular Biology of Bacteriophage T4*, J. D. Karam, ed., Washington, D.C., ASM Press, 1994, pp. 482-83.

FIG. 2B shows a Restriction Fragment Length Polymorphism (RFLP) Profile of *Salmonella* bacteriophage.

FIG. 3—FIG. 3 shows a protein profile of *Salmonella* bacteriophage on an SDS-PAGE gel.

Tables

Figure 2A:
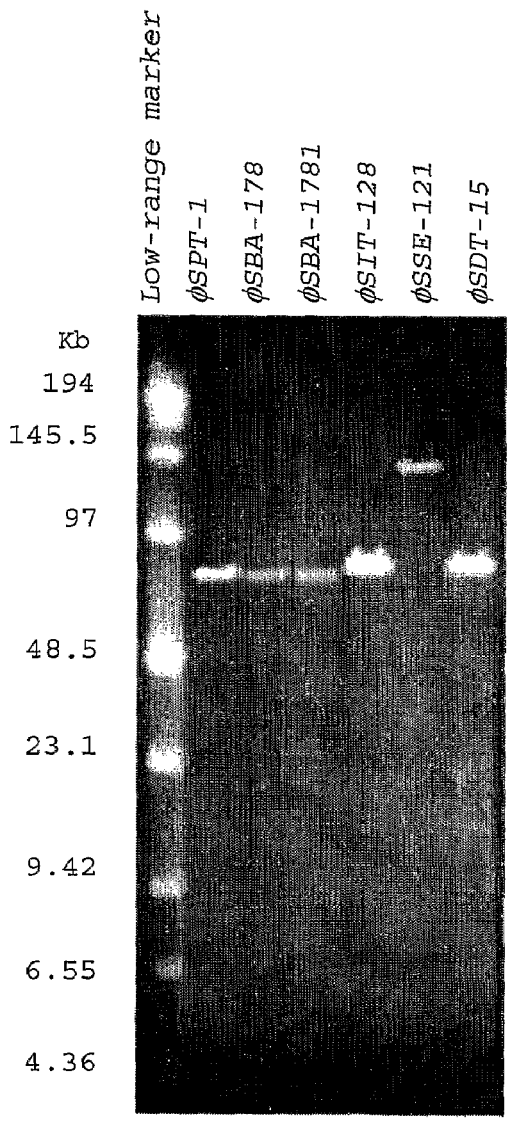
FIGS. 2A and 2B—FIG. 2A shows a Pulsed Field Gel Electrophoresis (PFGE) Profile of *Salmonella* bacteriophage.
Figure 2B:
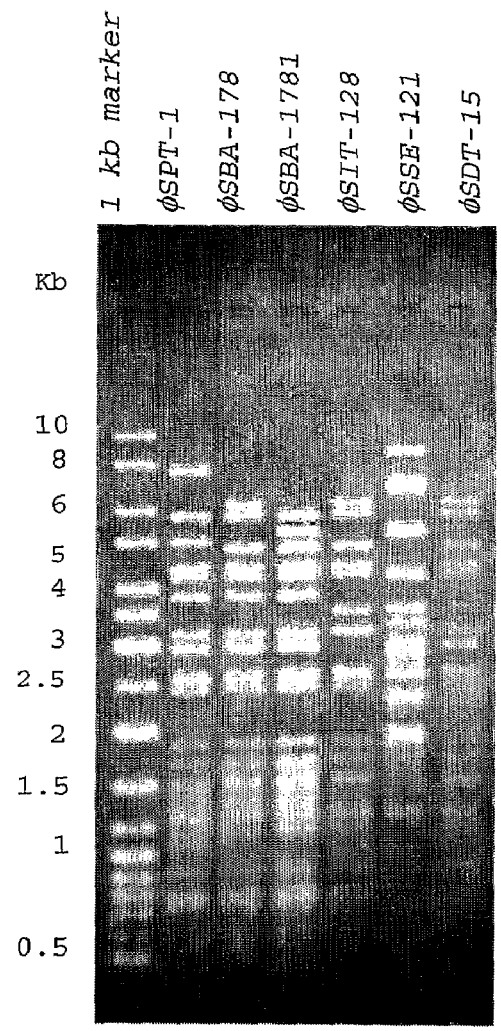

Table 1 shows a list of undesirable bacterial toxin genes.

Table 2 shows the lytic specificity of *Salmonella* bacteriophage for various *Salmonella* strains. *Salmonella* strains are listed in the left-hand column, and positive (+) or negative (−) lytic reactions for each *Salmonella* strain in the presence of *Salmonella* bacteriophage are listed in the right-hand column.

DETAILED DESCRIPTION OF THE EMBODIMENTS

Definitions

As used herein, "isolated" will mean material removed from its original environment (e.g., the natural environment in which the material occurs), and thus is "altered by the hand of man" from its natural environment. Isolated material may be, for example, foreign nucleic acid included in a vector system, foreign nucleic acid contained within a host cell, or any material which has been removed from its original environment and thus altered by the hand of man. Isolated material further encompasses isolated *Salmonella* bacteriophage or particular *Salmonella* bacterial isolates, isolated and cultured separately from the environment in which it was located, where these isolates are present in purified compositions that do not contain any significant amount of other bacteriophage or bacterial strains, respectively.

As used herein, "significant" will mean an amount of a substance present in the total measured composition, wherein the substance is present in greater than 1% of the total volume or concentration of the composition.

As used herein, "colonization" or "colonized" will refer to the presence of *Salmonella* on a foodstuff or environmental surface without perceptible significant alteration to that foodstuff or surface other than the presence of bacteria. The terms "colonization" and "colonized" stand in contrast to the terms "infection" or "infected" which are commonly understood to require perceptible deleterious alteration as part of their definition. "Colonization" and "colonized" may also refer to the presence of bacteria in or on a human or animal without perceptible damage, alteration, or disease.

As used herein, "ATCC" will mean the American Type Culture Collection, located at 10801 University Boulevard, Manassas, Va., 20110-2209, USA.

As used herein, "ORF" will mean an Open Reading Frame which is an in-frame sequence of codons that (in view of the genetic code) correspond to or encode a protein or peptide sequence. Two ORFs correspond to each other if the sequences or their complementary sequences encode the same amino acid sequences. An ORF sequence, operably associated with appropriate regulatory sequences, may be transcribed and translated into a polypeptide in vivo. A polyadenylation signal and transcription termination sequence will usually be located 3' to the coding sequence.

As used herein, "homology" will mean the degree of similarity between two nucleic acids (based on comparison of the chemical structure of the nucleic acids, as expressed by the sequence of nucleotides making up the nucleic acid or biologic function, as determined by whether two nucleic acids of minimum length 500 nucleotides and maximum length 10,000 nucleotides will hybridize to form a double-stranded complex). Similarity described functionally includes information on the conditions under which hybridization occurs, for example, two sequences are said to hybridize under highly stringent conditions when two single strands will hybridize when incubated in 0.1×SSC[1] at 65° C. Two sequences are said to hybridize under moderately stringent conditions when two single strands will hybridize when incubated in 1×SSC at 56° C. but not at higher temperatures. Two sequences are said to hybridize under low stringency conditions when two single strands will hybridize when incubated in 2×SSC at 50° C. but not at higher temperatures. Polynucleotide fragments which are tested for hybridization under the hybridization conditions recited above comprise, or alternatively consist of, polynucleotide fragments of about 10 kb or less in length, but greater than about 0.5 kb or more in length.

As used herein, "substantially pure" will mean a macromolecule essentially free of any similar macromolecules that would normally be found with it in nature. In other words, a substantially pure protein is in a composition that contains no more than 1% other proteins from the same taxonomic species. A substantially pure composition excludes media components, excipients or other non-contaminating compounds resulting from culturing, processing or formulating the composition.

[1] 20×SSC is 3 M NaCl, 0.3 M Na$_3$citrate.2H$_2$O, pH 7.0 at ambient temperature As used herein, "amplification" will mean the in vitro production of multiple copies of a particular nucleic acid sequence. The amplified sequence is usually in the form of DNA. A variety of techniques for carrying out such amplification are described in a review article by Van Brunt (1990, *Bio/Technol.*, 8(4):291-294). Polymerase chain reaction or PCR is a prototype of nucleic acid amplification, and use of PCR herein should be considered exemplary of other suitable amplification techniques. Other forms of amplification include, but are not limited to, ligase chain reaction (LCR) and gap-LCR.

*Salmonella* Bacteriophage

The invention provides novel *Salmonella* bacteriophage particles. In particular, this invention provides isolated *Salmonella* bacteriophage SPT-1, SBA-178, SBA-1781, SIT-128, SSE-121 and SDT-15, deposited on Jun. 24, 2003 with the ATCC and receiving ATCC Deposit Accession Nos. PTA-5281, PTA-5284, PTA-5282, PTA-5285, PTA-5283 and PTA-5280, respectively. Unless otherwise indicated, use of the term "*Salmonella* bacteriophage" in this application is intended to encompass each of the deposited bacteriophage, or mixtures of one or more up to all of them.

*Salmonella* bacteriophage has binding specificity for *Salmonella*, and is capable of lysing infected host *Salmonella* cells. Particularly preferred *Salmonella* bacteriophage have biological activity (e.g., the ability to lyse host *Salmonella* cells and/or the ability to produce phage progeny in a host cell). The invention further contemplates "variants" of *Salmonella* bacteriophage, which are bacteriophage having minor variation(s) in the genomic sequence and polypeptides encoded thereby while retaining the same general genotypic and phenotypic characteristics as the *Salmonella* bacteriophage. Variants of *Salmonella* bacteriophage encompass polymorphic variants. The invention also contemplates "derivative" bacteriophage, which are bacteriophage having modified genotypic or phenotypic characteristics relative to the deposited *Salmonella* bacteriophage. Derivative bacteriophage of the invention particularly encompass recombinantly designed *Salmonella* bacteriophage harboring genes encoding novel phenotypic traits. Such recombinant *Salmonella* bacteriophage are engineered to contain novel genes having traits not found in wild-type *Salmonella* bacteriophage. Variant *Salmonella* bacteriophage capable of performing the same or equivalent biological functions as *Salmonella* bacteriophage are particularly preferred.

The invention contemplates the use of *Salmonella* bacteriophage, or variants thereof to control the growth on, or colonization of, processed and unprocessed food products by *Salmonella*, or the colonization of buildings and equipment, particularly those associated with the processing of the same food product. The invention also provides methods of detecting the presence of *Salmonella* cells on processed or unprocessed food products, or equipment or buildings such as those involved in the processing of the same food products. The invention further provides methods of using *Salmonella* bacteriophage for the removal of antibiotic-resistant or other undesirable pathogens from medical, veterinary, animal husbandry, or any additional environments where they may be passed to humans or animals. The invention additionally provides for methods of using *Salmonella* bacteriophage to treat human and animal diseases caused by *Salmonella*. *Salmonella* bacteriophage are administered for the methods of the invention as a homogenous phage administration, or alternatively as a component of a multi-phage composition comprising numerous, related bacteriophage, all having lytic specificity for at least one *Salmonella* strain. These methods of use are provided with greater particularity infra.

Use of *Salmonella* Bacteriophage

Food Preservation

In one embodiment, the invention contemplates a method for the prevention of foodborne illnesses caused by the bacterium *Salmonella*, comprising contacting a food product or products with a microbial growth inhibiting effective amount of a bacteriophage composition comprising *Salmonella* bacteriophage. The modes of contact include, but are not limited to, spraying or misting the *Salmonella* bacteriophage composition on the food product(s), or by dipping or soaking the food product(s) in a solution containing a concentration of *Salmonella* bacteriophage sufficiently high to inhibit the growth of *Salmonella* or adding, injecting or inserting *Salmonella* bacteriophage into the food product(s).

In another embodiment, the invention contemplates the application of a *Salmonella* bacteriophage composition to equipment associated with the processing of food product(s), such as cutting instruments, conveyor belts, and any other implements utilized in the mass production of food products, including the preparation, storage and packaging steps of food processing. *Salmonella* bacteriophage can additionally be introduced into packaging materials used to contain food product(s), prior to or following transfer of the food product(s) to the packaging materials. Alternatively *Salmonella* bacteriophage is useful in the local processing of food products (e.g., in the home or in the restaurant kitchen), using the same modes of contact as described supra.

In another embodiment of the invention, *Salmonella* bacteriophage are added as a component of paper products, either during processing or after completion of processing of the paper products. Paper products to which *Salmonella* bacteriophage may be added include, but are not limited to, paper towels, toilet paper, moist paper wipes. In a preferred embodiment of the invention, *Salmonella* bacteriophage are added as a component of cleansing wipes. *Salmonella* bacteriophage may be added in an aqueous state to a liquid-saturated paper product, or alternatively may be added in powder form (e.g., lyophilized) to dry paper products, or any combination thereof. In similar manner, *Salmonella* bacteriophage may be incorporated into films such as those used for packaging foods, e.g., by impregnating or coating the film.

The methods of the invention further contemplate the application of *Salmonella* bacteriophage to the floors, walls, ceilings, drains, or other environmental surfaces in structures such as the industrial food processing or home environments. In a particularly preferred embodiment of the invention, *Salmonella* bacteriophage is applied to refrigerated devices used to store or transport food or food products, including but not limited to, home and industrial refrigerators, deli-meat and cheese counters, refrigerated trucks, and mobile food-service vehicles.

In a non-limiting embodiment of the invention, *Salmonella* bacteriophage of the invention are useful in preventing the colonization of, or inhibiting the growth of, *Salmonella* on processed or unprocessed food products by infecting, lysing or inactivating *Salmonella* present on said food product.

Processed or unprocessed food products in which *Salmonella* bacteriophage are particularly useful in preventing the growth or colonization of *Salmonella* include, but are not limited to, hot dogs, deli meats, luncheon meats, soft cheeses such as feta, Brie, Camembert, blue-veined cheeses, Mexican-style cheeses, pâtés, meat spreads, smoked seafoods such as salmon, trout, whitefish, cod, tuna or mackerel, poultry, salads, eggs, milk and dairy products, fish, shrimp, frog legs, yeast, coconut, sauces and salad dressing, cake mixes, cream-filled desserts and toppings, dried gelatin, peanut butter, chocolate, and ground beef.

*Salmonella* bacteriophage can also be administered with ready-to-eat foods and food products such as frankfurters and sliced deli meats.

Additional "ready to eat" foods to which *Salmonella* bacteriophage may be administered include, but are not limited to, cooked cured comminuted red meat products (such as beef and pork frankfurters); cooked cured comminuted poultry products (such as turkey frankfurters and chicken bologna); sliced cooked whole red meat muscle cuts, uninjected (such as sliced roast beef and sliced fresh ham prepared from minimally processed cuts); sliced cooked whole poultry muscle cuts, uninjected (such as sliced turkey breast and sliced chicken breast prepared from minimally processed cuts); sliced cooked cured whole red meat muscle cuts (such as corned beef and pastrami); sliced cooked cured whole poultry muscle cuts (such as turkey pastrami); injected whole red meat muscle cuts (such as ham and most processed and/or flavored whole muscle roast beef products); and injected whole poultry muscle cuts (such as most processed and/or flavored whole muscle chicken and turkey breast products.

*Salmonella* bacteriophage can also be administered to potable and non-potable water sources to reduce or eliminate the presence of *Salmonella*.

*Salmonella* bacteriophage compositions of the invention may be provided in aqueous or non-aqueous embodiments for the preservation of food. Aqueous embodiments of *Salmonella* bacteriophage include aqueous compositions comprising, or alternatively consisting of, *Salmonella* bacteriophage alone or in combination with other bacteriophage. Other bacteriophage include either bacteriophage specific for *Salmonella* or bacteriophage specific for other bacterial species, or both. Aqueous embodiments of *Salmonella* bacteriophage are available in solutions that include, but are not limited to, phosphate buffered saline, Luria-Bertani Broth or chlorine-free water.

Non-aqueous embodiments of *Salmonella* bacteriophage include, but are not limited to, lyophilized compositions or spray-dried compositions comprising, or alternatively consisting of, *Salmonella* bacteriophage alone or in combination with other bacteriophage.

*Salmonella* bacteriophage can be administered at a concentration effective to inhibit the growth or colonization of food or food products, as well as the equipment used to process or store food. In a non-limiting embodiment of the invention, *Salmonella* bacteriophage are typically administered at a growth inhibiting effective amount of a concentration of about $10^7$ to about $10^{11}$ Plaque Forming Units (PFU)/ml. One of skill in the art is capable of ascertaining bacteriophage concentrations using widely known bacteriophage assay techniques. *Salmonella* bacteriophage at such concentrations may be applied at, e.g., about 1 ml/500 cm$^2$.

Environmental Control

In another embodiment of the invention, *Salmonella* bacteriophage compositions are administered to environments to control the growth or viability of *Salmonella*, particularly the growth or viability of antimicrobial resistant strains of *Salmonella*. Antimicrobial resistant *Salmonella* include, but are not limited to, *Salmonella* showing resistance to ampicillin, amoxicillin/clavulanic acid, chloramphenicol, sulfamethoxazole/trimethoprim, ciprofloxacin, fluoroquinolones, enrofloxacin, clindamycin, penicillin, tetracyclin, pediocin PA-1, nisin A, and cephalosporins. Environments in which *Salmonella* bacteriophage is useful to control the growth or viability of *Salmonella* include, but are not limited to, medical facilities (including hospitals, out-patient clinics, school and/or university infirmaries, and doctors offices), veterinary offices, animal husbandry facilities, public and private restrooms, and nursing and nursing home facilities. The invention further contemplates the use of *Salmonella* bacteriophage for the battlefield decontamination of food stuffs, the environment, and personnel and equipment, both military and non-military.

*Salmonella* bacteriophage are additionally useful alone or in combination with other bacteriophage or other compounds, for controlling the growth of biofilms in aquatic environments. Other bacteriophage include either bacteriophage specific for *Salmonella* of bacteriophage specific for other bacterial species, or both. Aqueous embodiments of *Salmonella* bacteriophage are available in solutions that include, but are not limited to, phosphate buffered saline, Luria-Bertani Broth or chlorine-free water. In a particularly preferred embodiment, *Salmonella* bacteriophage is used to control biofilm growth in municipal and personal water systems, as well as biofilms present in refrigerated environments.

The modes of administration include, but are not limited to, spraying, hosing, and any other reasonable means of dispersing aqueous or non-aqueous *Salmonella* bacteriophage compositions, in an amount sufficiently high to inhibit the growth or viability of *Salmonella*. In a non-limiting embodiment of the invention, *Salmonella* bacteriophage are useful in preventing the growth or viability of *Salmonella* by infecting, lysing or inactivating *Salmonella* present in said environment. Administration of the *Salmonella* bacteriophage composition includes application to the floors, walls, countertops, ceilings, drains or any other environmental surface.

*Salmonella* Bacteriophage compositions of the invention are available in aqueous or non-aqueous embodiments for the treatment of various environments. Aqueous embodiments of *Salmonella* bacteriophage include aqueous compositions comprising, or alternatively consisting of, *Salmonella* bacteriophage alone or in combination with other bacteriophage. Aqueous embodiments of *Salmonella* bacteriophage are available in solutions that include, but are not limited to, phosphate buffered saline or chlorine-free water.

Non-aqueous embodiments of *Salmonella* bacteriophage include, but are not limited to, lyophilized compositions or spray-dried compositions comprising, or alternatively consisting of, *Salmonella* bacteriophage alone or in combination with other bacteriophage. Spray-dried compositions may include soluble and/or insoluble carrier materials as processing aids.

In another embodiment of the invention, *Salmonella* bacteriophage are added as a component of paper products, either during processing or after completion of processing of the paper products. Paper products to which *Salmonella* bacteriophage may be added include, but are not limited to, paper towels, toilet paper, moist paper wipes. In a preferred embodiment of the invention, *Salmonella* bacteriophage are added as a component of cleansing wipes. *Salmonella* bacteriophage may be added in an aqueous state to a liquid-saturated paper product, or alternatively may be added in powder form (e.g., lyophilized) to dry paper products, or any combination thereof.

*Salmonella* bacteriophage can be administered at a concentration effective to inhibit the growth or viability of *Salmonella* in a particular environment. In a non-limiting embodiment of the invention, *Salmonella* bacteriophage are administered at a concentration of about $10^7$ to $10^{11}$ PFU/ml. One of skill in the art is capable of ascertaining bacteriophage concentrations using widely known bacteriophage assay techniques.

Prevention or Treatment of Infection

In another embodiment, the invention contemplates a method for the prevention or treatment of illnesses caused by the bacterium *Salmonella*, comprising contacting a microbial growth inhibiting effective amount of a bacteriophage composition comprising *Salmonella* bacteriophage with a site or sites of infection of a host mammal infected with *Salmonella*.

The infected mammalian host may be a human host. *Salmonella* treatment of infected persons is particularly preferred in the treatment of immuno-compromised persons, pregnant females, and newborns and infants, who are all at an elevated risk of infection by *Salmonella*. The modes of contact include, but are not limited to, spraying or misting the *Salmonella* bacteriophage composition on the infected mammalian host, by injecting at a site or sites of infection a pharmaceutically acceptable composition containing a concentration of *Salmonella* bacteriophage sufficiently high to inhibit the growth of *Salmonella*, or by ingesting a solution containing a concentration of *Salmonella* bacteriophage sufficiently high to inhibit the growth of *Salmonella*. Additional routes of administration include but are not limited to oral, rectal, topical, ophthalmic, buccal, intravenous, otic, nasal, vaginal, inhalation, and intrapleural.

*Salmonella* Bacteriophage compositions of the invention are available in aqueous or non-aqueous embodiments for the treatment of infection. Aqueous embodiments of *Salmonella* bacteriophage include aqueous compositions comprising, or alternatively consisting of, *Salmonella* bacteriophage alone or in combination with other bacteriophage. Aqueous embodiments of *Salmonella* bacteriophage are available in solutions that include, but are not limited to, phosphate buffered saline or chlorine-free water.

Non-aqueous embodiments of *Salmonella* bacteriophage include, but are not limited to, lyophilized compositions or spray-dried compositions comprising, or alternatively consisting of, *Salmonella* bacteriophage alone or in combination with other bacteriophage. Spray-dried compositions may include soluble and/or insoluble carrier materials as processing aids.

*Salmonella* bacteriophage can be administered at a concentration effective to inhibit the growth or viability of *Salmonella* in the infected host. In a non-limiting embodiment of the invention, *Salmonella* bacteriophage are administered at a concentration of about $10^7$ to $10^{11}$ PFU/ml. One of skill in the art is capable of ascertaining bacteriophage concentrations using widely known bacteriophage assay techniques.

Depending on the severity of pecularities of the infection, *Salmonella* bacteriophage can be administered to humans (i) orally, in tablet or liquid formulation ($10^5$-$10^{11}$ PFU/dose), (ii) rectally, (iii) locally (skin, eye, ear, nasal mucosa, etc.), in tampons, rinses and creams, (iv) as aerosols or intrapleunal injections and (v) intravenously.

Production of *Salmonella* Bacteriophage

*Salmonella* bacteriophage are produced using a culture system. More specifically, host *Salmonella* are cultured in batch culture, followed by inoculation of the *Salmonella* culture with an appropriate inoculum of *Salmonella* bacteriophage. Following incubation, the *Salmonella* bacteriophage are harvested and filtered to yield phage progeny suitable for the uses enumerated herein.

The invention provides compositions comprising active viral particles of *Salmonella* bacteriophage capable of lysing *Salmonella* strains.

The concentration of *Salmonella* bacteriophage may be determined using phage titration protocols. The final concentration of *Salmonella* bacteriophage can be adjusted by dilution with buffer to yield a phage titer of $10^{10}$ to $10^{11}$ PFU/ml. The resulting *Salmonella* bacteriophage composition can be freeze or spray-dried for storage. Upon reconstitution, the phage titer can be verified using phage titration protocols and host *Salmonella* bacteria. One of skill in the art is capable of determining bacteriophage titers using widely known bacteriophage assay techniques (e.g., Davis et al., "Microbiology, $3^{rd}$ Ed.", Harper & Row, Hagerstown, 1980, pp. 874-877, 880-883).

Polynucleotides

Polynucleotides and Variants thereof

The invention contemplates isolated polynucleotide molecules of the *Salmonella* bacteriophage, contained within bacteriophage deposits submitted with the ATCC and receiving ATCC Deposit Accession Nos. PTA-5281, PTA-5284, PTA-5282, PTA-5285, PTA-5283 and PTA-5280.

Polynucleotides of the invention encompass polyribonucleotide and polydeoxyribonucleotide, including modified or unmodified RNA or DNA. Polynucleotides of the invention can derive from genomic DNA, as well as cDNA, mRNA and synthetic polynucleotide sequences. One of ordinary skill in the art is well aware of techniques for generating cDNA sequence from mRNA sequence. Polynucleotides of the invention comprise single or double-stranded DNA or RNA sequences, as well as DNA/RNA hybrids.

Polynucleotides of the invention also encompass modified polynucleotides, such as for example phosphorothioated DNAs or PNAs (Peptide Nucleic Acids). Additionally, polynucleotides of the invention may include one or more labels (e.g., radioactive label, biotin, fluorescent label, chemiluminescent or colorimetric label) for diagnostic or tracking and monitoring purposes.

Polynucleotide Fragments

The invention further contemplates fragments of the polynucleotides discussed supra. Polynucleotide fragments are particularly useful for the detection of Salmonella bacteriophage. Using DNA isolation techniques known in the art or described herein (i.e., CsCl gradients, Pulse Field Gel Electrophoresis), one of skill is capable of using the polynucleotide isolation techniques to obtain Salmonella bacteriophage DNA, from which polynucleotide fragments are generated. Numerous techniques for generating polynucleotide fragments are also widely known in the art (e.g., Restriction Digests, Pressure-shearing via French Press, etc.). Fragments can be isolated via gel electrophoresis or other means and radioactively or non-radioactively labeled for use as probes. DNA fragments can also be purified using HPLC. Labeled polynucleotide fragments are useful under stringent hybridization conditions to identify Salmonella bacteriophage from a bacteriophage culture or environmental surface. Kits are widely available in the art for labeling polynucleotide fragments (See Invitrogen product catalog, Sigma-Aldrich product catalog).

Polypeptides

Polypeptides and Variants Thereof

The invention further encompasses polypeptides encoded by the polynucleotides of the invention, contained within ATCC Deposit Accession Nos. PTA-5281, PTA-5284, PTA-5282, PTA-5285, PTA-5283 and PTA-5280, Polypeptides of the invention may encompass viral coat proteins, transcriptional regulatory proteins, and virulence proteins.

Polypeptides of this invention are molecules having an amino acid sequence encoded by polynucleotides of the invention as broadly defined. Polypeptides encompasses proteins, peptides and fragments thereof (functional or non-functional) encoded by Salmonella bacteriophage polynucleotides. Preferred polypeptides of the invention comprise, or alternatively consist of, antigenic and/or immunogenic polypeptides, especially antigenic and/or immunogenic polypeptide fragments.

Derivative Salmonella Bacteriophage

Polynucleotides of the invention are also useful for the production of derivative Salmonella bacteriophage, particularly recombinant Salmonella bacteriophage. In one embodiment of the invention, homologous recombination techniques are used to introduce homologous sequences encoding alternative proteins, non-functional proteins, or non-coding sequences into the Salmonella bacteriophage DNA sequence. Such techniques are useful to "knock-out" undesired traits of the Salmonella bacteriophage, or alternatively to introduce different traits. In a particularly preferred embodiment of the invention, homologous recombination is used to "knock-out" ORFs encoding proteins that are putatively involved in a lysogenic cycle of the Salmonella bacteriophage.

In another embodiment of the invention, the invention provides recombinant Salmonella bacteriophage having novel bacteriophage genes introduced into the Salmonella bacteriophage sequence. In this embodiment, the double-crossover (homologous recombination) methods of Loessner et al. (incorporated herein by reference in its entirety) are utilized to introduce a novel bacteriophage gene(s) into the genome of Salmonella bacteriophage. Successful recombinant Salmonella bacteriophage replicate in the host Salmonella cell, producing recombinant progeny phage.

In certain embodiments of the invention it is important to confirm that bacteriophage cocktails contain "lytic" phage rather than "lysogenic" phage, as some lysogenic phages (i.e., transducing phages) may be capable of transferring "undesirable" bacterial genes (e.g., genes encoding bacterial toxins) from one bacterial host to another. Therefore, the use of lysogenic phage on an industrial scale could increase the risk of acquisition of "undesirable" genes from new bacterial strains, which could contribute to the emergence of new pathogenic bacteria. It is therefore prudent to make efforts to avoid or minimize the use of phage, either in agribusiness or in human therapeutic settings, that (i) contain genes directly associated with bacterial virulence (so that additional virulence genes are not introduced into the environment) and/or (ii) can significantly contribute to the horizontal transfer of virulence-associated genes between bacterial species or strains (to minimize the risk of phage-mediated transduction of undesirable genes). Accordingly, in an alternative embodiment of the invention homologous recombination is used to "knock-out" undesirable genes such as bacterial toxin genes, or genes having significant homology thereto, found in Salmonella bacteriophage DNA. A list of undesirable bacterial toxin genes is provided in Table 1.

TABLE 1

Undesirable (e.g., Bacterial toxin) Genes known to be carried by Transducing Bacteriophages

| Toxin and its Encoding Gene | Bacterial Pathogen | Reference |
| --- | --- | --- |
| Enterotoxin A (entA) | Staphylococcus aureus | Betley and Mekalanos, 1988 |
| Enterotoxin A (sea, sel) | Staphylococcus aureus | Betley and Mekalanos, 1985 |
| Enterotoxin A (sea) | Staphylococcus aureus | Kuroda et al., 2001 |
| Staphylokinase (sak) | Staphylococcus aureus | Coleman et al., 1989 |
| Enterotoxin P (sep) | Staphylococcus aureus | Kuroda et al., 2001 |
| Exfoliative toxin A (eta) | Staphylococcus aureus | Yamaguchi et al., 2000 |
| Diphtheria toxin (tox) | Corynebacterium diphtheriae | Freeman, 1951 |
| Shiga toxins (stx1,2) | Escherichia coli | O'Brien et al., 1984 |
| Cytotoxin (ctx) | Pseudomonas aeruginosa | Nakayama et al., 1999 |
| Cholera toxin (ctxA) | Vibrio cholerae | Waldor & Mekalanos, 1996 |
| Cholera toxin (ctxB) | Vibrio cholerae | Waldor & Mekalanos, 1996 |
| Zonula occludens toxin (zot) | Vibrio cholerae | Koonin, 1992 |

TABLE 1-continued

Undesirable (e.g., Bacterial toxin) Genes known to be carried by Transducing Bacteriophages

| Toxin and its Encoding Gene | Bacterial Pathogen | Reference |
| --- | --- | --- |
| Neurotoxin (C1) | *Clostridium botulinum* | Barksdale and Arden, 1974. |
| Enterohaemolysin (hly) | *Escherichia coli* | Beutin et al., 1993 |
| Streptococcal exotoxin A (speA) | *Streptococcus pyogenes* | Weeks and Ferretti, 1984 |
| Streptococcal exotoxin C (speC) | *Streptococcus pyogenes* | Goshorn and Schlievert, 1989 |
| Streptococcal exotoxin K (speK) | *Streptococcus pyogenes* | Beres et al., 2002 |

In another embodiment of the invention, homologous recombination is used to introduce or knock-out genes involved in burst size. For example, homologous recombination is used to introduce alternative bacteriophage genes which delay the burst event or increase the phage burst size.

References disclosing alternative bacteriophage genes involved in the timing of the burst event or the size of the phage burst include, but are not limited to, Wang I N, Smith D L, Young R. (2000), Holins: the protein clocks of bacteriophage infections, *Annu. Rev. Microbiol.;* 54:799-825; Johnson-Boaz R, Chang C Y, Young R. (1994), A dominant mutation in the bacteriophage lambda S gene causes premature lysis and an absolute defective plating phenotype, *Mol. Microbiol.,* 13(3):495-504.

Recombinant *Salmonella* Bacteriophage Reporter Systems

In another embodiment of the invention, recombinant *Salmonella* bacteriophage harboring a reporter system(s) are generated using polynucleotides of the invention. *Salmonella* bacteriophage reporter systems of the invention are useful for the detection of the presence of viable *Salmonella* cells to which the bacteriophage have specificity. Following the techniques of Loessner et al., for example, one of skill in the art can generate recombinant *Salmonella* reporter bacteriophage (Loessner et al., Appl. Environ. Micro., 62(4):1133-1140 (1996)). For example, the *Vibrio harveyi* luxAB gene may be introduced into the *Salmonella* bacteriophage DNA sequence using techniques such as homologous recombination. An ideal target for the introduction of the luxAB gene is immediately downstream and in frame with a ORF encoding a *Salmonella* bacteriophage capsid protein, thereby creating a sequence encoding a fusion protein. The preferable location of introduction of the luxAB gene sequence is particularly before any sequence encoding a transcriptional terminator downstream of the ORF encoding a capsid protein. Other *Salmonella* bacteriophage ORF sequences which may function as useful sources of luxAB gene-fusions include gene sequences encoding tail-sheath proteins, or any other late gene region sequences encoding phage head or tail proteins. Such information can be determined using the polynucleotides isolated from ATCC Deposit Accession Nos. PTA-5281, PTA-5284, PTA-5282, PTA-5285, PTA-5283 and PTA-5280 and obtaining and analyzing sequence data derived therefrom. Recombinant polynucleotides harboring the reporter gene are used to generate progeny phage harboring the reporter gene, and expressing the reporter gene-fusion.

Successful recombinant phage are subsequently screened using a luciferase assay in which *Salmonella* bacteriophage (in lysates, for example) containing the luciferase-reporter fusion protein are mixed with a *Salmonella* culture, and cultured for a fixed period of time (e.g., 90 to 120 minutes). Samples are then assayed for bioluminscence using a tube luminometer. Successful recombinant *Salmonella* bacteriophage expressing the reporter fusion protein in the presence of viable *Salmonella* are isolated and cultured to appropriate concentrations to allow for the isolation and storage of said recombinant bacteriophage. The resulting recombinant *Salmonella* bacteriophage may be used with methods of the invention to detect the presence of viable *Salmonella*.

In addition to the *Vibrio harveyi* luxAB gene, other reporter genes which are useful for the generation of *Salmonella* reporter bacteriophage include, but are not limited to, the firefly luciferase gene.

The invention further contemplates the introduction of one or more of the above-described recombinant events. For example, a recombinant *Salmonella* bacteriophage of the invention may harbor a reporter gene as well as lack a gene associated with the lysogenic cycle.

Use of *Salmonella* Bacteriophage Polynucleotides and Polypeptides therefrom Polypeptides such as *Salmonella* bacteriophage lytic enzymes encoded by polynucleotides of the invention are used for applications designed to prevent the growth of *Salmonella* through cell wall lysis. In this context, lytic polypeptides are useful for the prevention of the growth of *Salmonella* on processed and unprocessed food products, as well as equipment used for the processing of said food products.

In another preferred embodiment of the invention, *Salmonella* bacteriophage lytic polypeptides are useful for the treatment of one or more infections in a mammal, including humans, by administering a therapeutically effective amount of a *Salmonella* bacteriophage lytic enzyme to the patient. This method is useful for the treatment of *Salmonella* infections of the gastrointestinal system. Similarly, this method is useful in a prophylactic setting for the prevention of infection by *Salmonella* in pregnant mammals, including humans. This method of treatment is further useful for the prevention or other disorders or infections caused by *Salmonella*, such as salmonellosis, gastroenteritis and typhoid fever.

Detection Systems

*Salmonella* bacteriophage poynucleotides are particularly preferred in a method of detecting the presence of *Salmonella* bacteriophage. For example, fragments of at least 20 nucleotides in length are useful as probes for the identification of the presence of *Salmonella* bacteriophage in an environmental or food sample using hybridization techniques. Using stringent hybridization techniques, one skilled in the art can determine the presence of *Salmonella* bacteriophage in a sample.

In another embodiment of the invention, polynucleotide fragments of between about 16 and about 40 nucleotides in length are useful as primers for the identification of the presence of *Salmonella* bacteriophage in, e.g., an environmental or food sample using PCR amplification techniques. These applications are particularly useful in the sense of determining the presence of *Salmonella* bacteriophage in food over extended periods of time following treatment of the food with *Salmonella* bacteriophage. PCR amplification conditions may vary, but one skilled in the art can readily determine the appropriate PCR amplification conditions (See, e.g., *Current Protocols in Molecular Biology*, Frederick M. Ausubel, et al., ed., Wiley-Interscience, NY, 1989 and periodic updates thereof).

Alternatively, recombinant *Salmonella* bacteriophage themselves, such as for example the *Salmonella* luciferase reporter bacteriophage described supra, are useful in methods of screening food products and food processing equipment for the presence of viable *Salmonella*. In such a system, *Salmonella* bacteriophage containing a reporter system (such as, for example, a luciferase reporter system) are applied to the sample and analyzed at some time point in the future for the activation of the reporter molecule. The activation of the reporter molecule is indicative of the presence of viable *Salmonella* cells.

In a preferred embodiment of the invention, *Salmonella* bacteriophage polynucleotides or fragments thereof are useful as probes to detect the presence of *Salmonella* bacteriophage. In another embodiment of the invention, *Salmonella* bacteriophage polynucleotides or fragments thereof are useful as part of a process for the detection of *Salmonella* bacteriophage during production of the same. Alternatively, *Salmonella* bacteriophage polynucleotides or fragments thereof are useful for the detection of the presence of *Salmonella* bacteriophage introduced into foodstuffs or packaging materials for the same during part of a production method for the production or packaging of food stuffs. In an additional embodiment of the invention, more than one labeled *Salmonella* bacteriophage polynucleotide fragment is used as a probe to detect the presence of *Salmonella* bacteriophage in a sample. Polynucleotide fragments of the invention useful for the detection of *Salmonella* bacteriophage are preferably at least 20 nucleotides in length. Polynucleotide fragments of the invention are also useful for the detection of closely related *Salmonella* bacteriophage isolates under stringent or non-stringent hybridization conditions. Polynucleotides fragments of the invention may include one or more labels (e.g., radioactive label, biotin, fluorescent label, chemiluminescent or colorimetric label) for diagnostic or tracking and monitoring purposes.

In another embodiment of the invention, polynucleotides and polypeptides of the invention, or fragments thereof, are used in techniques to identify *Salmonella* bacteriophage. By way of the following non-limiting list of experimental techniques, one skilled in the art can easily identify bacteriophage compositions as comprising *Salmonella* bacteriophage when the same techniques are performed on a comparative basis against the bacteriophage deposited in ATCC Deposit Accession Nos. PTA-5281, PTA-5284, PTA-5282, PTA-5285, PTA-5283 and PTA-5280, The experimental techniques that can be used include, but are not limited to, DNA sequencing; Polymerase Chain Reaction (PCR) with sequence-specific primers; Southern blot DNA hybridization with sequence-specific nucleic acid probes; Restriction Fragment Length Polymorphism (RFLP) analysis; SDS-Polyacrylamide Gel Electrophoresis analysis of raw protein extracts; SDS-Polyacrylamide Gel Electrophoresis analysis of raw protein extracts with protein sequencing by any means available; Peptide mapping experiments; 2D-gel electrophoresis profiles; and Western blot analysis using polyclonal antibody preparation(s). These and other useful techniques are fully enabled by the deposited bacteriophage in view of the present specification and laboratory references such as *Current Protocols in Molecular Biology*, Frederick M. Ausubel, et al., ed., Wiley-Interscience, NY, 1989 and periodic updates thereof; Sambrook, et al., *Molecular Cloning: A Laboratory Manual*, $3^{rd}$ Ed., 2001; and Coligan, et al., eds., *Current Protocols in Protein Science*, Wiley, Brooklyn, N.Y., 2001 and periodic updates thereof, each of which are incorporated herein by reference.

Epidemiological Typing

*Salmonella* bacteriophage of the invention are further useful as a tool for the epidemiological typing of *Salmonella* isolates. For example, one of skill in the art can use *Salmonella* bacteriophage of the invention to screen a panel of *Salmonella* isolates to aid in the taxonomic identification of the *Salmonella*, by determining which isolates yield a positive lytic reaction to the *Salmonella* bacteriophage. (See, for example, Mee-Marquet et al., Appl. Env. Micro., 63(9):3374-3377 (1997)). *Salmonella* bacteriophage can be combined with other *Salmonella* specific bacteriophage to further refine the epidemiological typing results. The specificity of the *Salmonella* bacteriophage for certain strains of *Salmonella* demonstrates the utility of *Salmonella* bacteriophage as an epidemiological typing tool.

EXAMPLES

Example 1

*Salmonella* Bacteriophage Isolation

*Salmonella* bacteriophage were isolated from Baltimore Inner Harbor waters (isolates SIT-128; SSE-121) and Baltimore sewage effluent (isolates SPT-1; SBA-178; SDT-15; SBA-1781) using lysis of *Salmonella* to form plaques in bacterial lawns as a means of detecting the presence of bacteriophage having lytic specificity for *Salmonella*. Plaques are harvested, diluted, and re-plated on bacterial lawns through a process of serial enrichment until a single bacteriophage species, or monophage, results as determined by a stable restriction fragment length profile of the bacteriophage DNA. The isolates obtained using the technique recited supra may be cultured using the techniques as set forth herein. *Salmonella* bacteriophage was deposited with the ATCC, receiving ATCC Deposit Accession Nos. PTA-5281, PTA-5284, PTA-5282, PTA-5285, PTA-5283 and PTA-5280.

PFU concentration of the *Salmonella* bacteriophage may be determined using techniques known in the art, such as for example, the lytic reaction described by Marquet-Van der Mee, N., and A. Audurier (Appl. Environ. Micro., 61(1):303-309 (1995)), herein incorporated by reference. Briefly, host *Salmonella* cells are inoculated into tryptose phosphate broth (Difco) and incubated at 30° C. until the onset of log phase growth (approximately 3 to 5 hours). Culture plates are then inoculated by flooding of the surface of the tryptose agar or Luria-Bertani Broth Agar (Difco) with 2 to 3 mls of the broth culture. After removal of the surplus inoculum, the plates are allowed to dry for at least 30 min. at 37° C. The phage preparations are then applied to the seeded agar plates. The plates are incubated overnight at 30° C. The determination of the lytic specificity of *Salmonella* bacteriophage for a particular *Salmonella* strain is determined by observing the plates for clear plaques on a lawn of bacterial growth.

Example 2

Production of *Salmonella* Bacteriophale Lysate in Liquid Culture

*Salmonella* Bacteriophage Culturing

Single aliquots of *Salmonella*, stored in 70% LB broth/30% glycerol medium, were revived from a −80° C. freezer. The *Salmonella* culture was allowed to thaw at room temperature for 15-30 min., followed by brief vortexing. 10 ml of *Salmonella* was inoculated into 35 ml of LB-broth medium, and cultured at 30° C. at 150 rpm over-night on a rotary shaker. The resulting O.D.$_{600}$ of the culture was approximately 0.3-0.4.

10 ml of *Salmonella* was inoculated into 100 ml of LB-broth medium, and cultured at 30° C. at 150 rpm for approximately 2-2.5 hours, until the OD$_{600}$ reaches 0.1. To this culture was added a total of approximately $10^9$ PFU of *Salmonella* bacteriophage. (PFU of the *Salmonella* bacteriophage was confirmed before-hand).

The mixture was then transferred to a 2 L flask containing 1.0 L of M9 medium supplemented with 20% glucose, 1 M MgSO$_4$, and 1 M CaCl$_2$. The mixture was cultured at 30° C. at 150 rpm for approximately 5-7 hours, until the OD$_{600}$ reaches 0.04-0.01. At this point, *Salmonella* bacteriophage were harvested and purified.

Alternatively phage propagation can be carried out in 1 to 5 L flasks containing appropriate liquid microbiologic media, or in fermenters containing appropriate liquid microbiologic media. Batch fermentation is carried out in sterilized fermentation equipment in volumes ranging from 5 to 2,500 liters. A volume of an overnight culture in LB (or similar rich bacteriological medium free of animal derivatives such as bovine albunin; e.g., terrific broth) of the desired host strain of *Salmonella* is incubated with a pre-determined optimal volume of *Salmonella* bacteriophage seed stock. Fermentation is carried out at 30° C. to 37° C. for 5-7 h with periodic or continuous monitoring of the OD$_{600}$ until optimal lysis and phage yield for each host-bacteriophage pair has occurred. *Salmonella* strains which are lysed by the respective phage may be used for propagation (See Table 2). Each of the 6 *Salmonella* bacteriophage have lytic specificity for *Salmonella typhimurium* strain 13311, which can be obtained from the ATCC using ATCC Deposit Accession No. 13311. *Salmonella* bacteriophage SSE-121 has lytic specificity for *Salmonella* strain ATCC 13076, which can be obtained from the ATCC using ATCC Deposit Accession No. 13076.

Bacterial cell suspensions containing phage are cleared of bacteria and bacterial fragments by either low speed centrifugation (usually employed for batches <10 liters), or by tangential flow filtration (usually employed for batches >10 liters). Low speed centrifugation is carried out at 8,000×g for 30 min at 4° C. Supernatant fluids containing *Salmonella* bacteriophage are then filtered through an inert 0.45 µm pore size filter, and processed as described below (step #2 and thereafter). Instead of centrifugation, larger volumes are:

(1) cleared of bacteria and bacterial debris by tangential flow filtration through 0.22 µk Durapore (Millipore, Inc., Bedford, Mass.) PVDF (or essentially equivalent) filter.

(2) All filtrates are next treated with DNAse and RNAse, each at concentrations of 0.75 mg/L for 30-60 min at room temperature.

(3) Following nuclease digestion, the bacteriophage are collected, washed, concentrated, and exchanged into phosphate-buffered saline by tangential flow filtration using a 50 KDA Polyethersulforne (e.g., Biomax 50 KDA, Millipore, Inc)—or essentially equivalent filter. The tangential flow filtration process removes medium components, digested nucleic acids, and the nucleases.

(4) The 50 kDa filtration is then followed by filtration through an inert 0.22 µM filter. Batches are handled aseptically following the 0.22 µM filtration.

The concentration of *Salmonella* Bacteriophage is determined by titration. The concentration of *Salmonella* bacteriophage is adjusted to a specific concentration between $10^{10}$ to $10^{11}$ PFU/ml by dilution with buffer or by concentration by tangential flow filtration. The lytic activity of the final product is then determined by titration. Titrations are highly accurate and reproducible when performed against a single *Salmonella* Bacterial strain, but not when performed against a mixed culture of strains. The final titer of *Salmonella* Bacteriophage is calculated.

Following titration, *Salmonella* bacteriophage is freeze- or spray-dried after addition of 10% skim milk. An appropriate volume of diluent may be added to achieve the specified final working concentration. The required volume can be validated for each lot of *Salmonella* Bacteriophage by reconstitution of test samples and determination of the lytic titer of the bacteriophage determined as described above.

Example 3

Alternative Production of *Salmonella* Bacteriophage Lysate in Liquid Culture

Shake flask batches of each phage were carried out in 2-L flasks. *Salmonella enterica* strains were grown in LB broth overnight at 37° C., subcultured and grown to an OD$_{600}$ of 0.2-0.3. Growth was monitored spectrophotometrically until lysis occurred and phage harvested by vacuum filtration (Stericup, Millipore). Triplicate batches of each phage were concentrated separately and buffer exchanged with PBS by tangential-flow filtration in a Pellicon 2 Mini Cassette using a 50 kDa filter (Millipore). High titer master and working stocks of each monophage were made in liquid cultures. Cultures of the appropriate *Salmonella enterica* host strain were grown in LB broth to an OD$_{600}$ of 0.2-0.3. Growth was monitored spectrophotometrically, following lysis, phage were sterile filtered (0.22 µm Stericup, Millipore) and treated with DNase I and RNase A to a final concentration of 1 µg/ml for 30 min at room temperature. Phage were harvested by centrifugation (31,000×g, 2 h), aliquoted into amber glass vials and stored at 4° C.

Large-scale batches of each phage were generated in a 10-L Bioflo 110 fermenter (New Brunswick Scientific Co., Edison, N.J.) containing 10 L of LB broth inoculated with 100 ml of an actively growing seed culture after the OD$_{600}$ of the culture was approximately 1.0. The fermentation was maintained at a temperature of 37° C., with an aeration rate of 3-7 liters/min (pH 7.0) and a dissolved oxygen level of 30%. The pH was controlled by addition of 1.2 N phosphoric acid or 1 N NaOH, and foaming was controlled by addition of antifoam 204 (Sigma) as needed. Cultures were infected at an MOI of 0.005-0.5 when the OD$_{600}$ reached 0.15-0.2. Phage was harvested at 3-4 h post-infection by tangential-flow filtration in a Pellicon 2 Mini Cassette using a 0.2 µm filter (Millipore). Phage was concentrated to a volume of 1 L and buffer exchanged with PBS by tangential-flow filtration in a Pellicon 2 Mini Cassette using a 50 kDa filter (Millipore).

Example 4

Application of *Salmonella* Bacteriophage for the Preservation of Food Products

*Salmonella* bacteriophage produced using the methods of the present invention may be dispersed in an appropriate aqueous solution or lyophilized or freeze-dried powder and applied to the surface of food products. Alternatively, *Salmonella* bacteriophage may be included with a cheese culture or other microbially active foodstuff prior to or during processing. The *Salmonella* bacteriophage are cultured for a period of time on the surface of the food product or within the food product.

Example 5

Isolation of *Salmonella* Bacteriophage DNA

In order to isolate *Salmonella* bacteriophage DNA, 0.75 ml of phage in phosphate-buffered saline solution (at a titer of $10^8$-$10^{11}$ PFU/ml) was collected. To this phage were added 10 µl of Proteinase K (20 mg/ml) and 2 µl of RNAse (10 mg/ml), followed by incubation at 37° C. for 30 minutes, and a subsequent incubation at 56° C. for 30 minutes. Following incubation, 75 µl of a mixture of 10% SDS (0.1 ml), 0.5 M EDTA (0.1 ml) and 0.8 ml of water was added and incubated at room temperature for 5 min. 0.75 ml of a phenol:chloroform:isoamylalcohol (25:24:1) solution was mixed well with the sample, followed by centrifugation at 13,000 RPM for five (5) min.

Next, the supernatant was carefully removed (approximately 600 µl), and transferred to a clean eppendorf tube. 0.6 ml of chloroform was added to the supernatant, mixed well, and centrifuged at 13,000 RPM for five (5) min. The supernatant was then carefully extracted (approximately 500 µl).

Next, 0.1 volumes of 3M sodium acetate (40 ml) was added to the solution, followed by 2.5 volumes of cold 95% ethanol (1 ml) to precipitate the *Salmonella* bacteriophage DNA. The solution was allowed to incubate at −20° C. for 1 hour, followed by centrifugation at 13,000 RPM for thirty (30) min.

Following centrifugation, the pellet was washed with 1 ml of 70% cold ethanol, and the supernatant was poured from the pellet. The pellet was allowed to air dry, and was then resuspended in 36-360 µl of TE (10 mM tris-HCL, pH=85, 1 mM EDTA).

Example 6

Restriction Fragment Length Polymorphism (RFLP) Profile

DNA was isolated from *Salmonella* bacteriophage using Qiagen Plasmid Miniprep or Midiprep kits (Valencia, Calif.) according to the manufacturer's directions. Briefly, the instructions are as follows:

Harvest a desired quantity of *Salmonella* bacteriophage by centrifugation at 30,000×g for 2 to 3 h at 4° C. Resuspend the pelleted *Salmonella* bacteriophage in 250 µl Buffer P1 (10 mM tris-HCl, pH=8, 100 µg/ml RNaseA) and transfer to a microcentrifuge tube. Ensure that 100 µl/ml RNase A has been added to Buffer P1. No cell clumps should be visible after resuspension of the pellet. Add 250 µl of Buffer P2 (0.2 M NaOH, 2% SDS) and gently invert the tube 4-6 times to mix. Do not vortex, as this will result in shearing of genomic DNA. If necessary, continue inverting the tube until the solution becomes viscous and slightly clear. Do not allow the lysis reaction to proceed for more than 5 min.

Add 350 µBuffer N3 (4.2M guanidine HCL, 0.9M potassium acetate, pH=4.8) and invert the tube immediately but gently 4-6 times. To avoid localized precipitation, mix the solution gently but thoroughly, immediately after addition of Buffer N3. The solution should become cloudy. Centrifuge for 10 min at maximum speed in a tabletop microcentrifuge. A compact white pellet will form. Apply the supernatants to a plasmid DNA isolation spin column containing silica gel (i.e., "QIAprep® column") by decanting or pipetting. Centrifuge for 30-60 s. Discard the flow-through.

Wash the QIAprep column by adding 0.5 ml Buffer PB (5M guanidine HCL, 30% isopropanol) and centrifuging for 30-60 s. Discard the flow-through. Wash QIAprep column by adding 0.75 ml Buffer PE (80% ethanol/water) and centrifuging for 30-60 seconds.

Discard the flow-through to allow for complete removal of the residual wash buffer, and centrifuge for an additional 1 min to remove residual wash buffer. Residual ethanol from Buffer PE may inhibit subsequent enzymatic reactions. Place the QIAprep column in a clean 1.5 ml microcentrifuge tube. To elute DNA, add 50 µl Buffer EB (10 mM Tris.Cl, pH=8.5) or water to the center of each QIAprep column, let stand for 1 min, and centrifuge for 1 min. Substantially equivalent procedures are followed for isolation of bacteriophage DNA using the larger scale midi-prep kit.

In order to perform the RFLP experiment with the isolated *Salmonella* bacteriophage DNA, the following protocol is followed.

(1) Quantitate the DNA by Absorbance at 260 nm., and aliquot in a microcentrifuge tube 0.5-1 µg DNA per *Salmonella* bacteriophage sample to be tested. Add 10 units SpeI and mix, followed by an incubation at 37° C. for 2 hours.

(2) Add tracking dye (bromophenol blue+xylene cyanol) and separate on a 1.0% agarose gel at 80 to 100 V for 50 min. Stain with ethidium bromide. Digestion with one or more additional enzymes (HindIII, and/or EcoRV, and/or EcoRI) may be used if the RFLP patterns using SpeI patterns are identical, in order to provide additional confirmation of identity.

Example 7

Lytic Specificity of *Salmonella* Bacteriophage

One hundred eighty-seven *Salmonella enterica* strains representing serotypes Enteritidis, Typhimurium, Hadar, Newport, Agona, Kentucky and Heidelberg were screened for their susceptibility to the *Salmonella* bacteriophage by the drop on lawn method. Strains were streaked onto LB agar plates and incubated at 37° C. overnight. One colony of each strain was inoculated into a separate well of a 96-well microtiter plate containing LB broth and incubated at 37° C. until the $OD_{600}$ reached 0.2-0.3. One hundred microliters of each strain were mixed with LB soft agar and poured onto an LB agar plate. After the soft agar hardened 10 µl of each phage were spotted in triplicate onto the plates inoculated with the *S. enterica* strains. Lytic activity was observed after overnight incubation at 37° C. Lytic specificity results are presented in Table 2.

TABLE 2

Lytic specificity of *Salmonella* bacteriophage for various *Salmonella* isolates.

| Serotype | Strain# | SPT-1 | SSE-121 | SIT-128 | SBA-178 | SBA-1781 | φSDT-15 |
|---|---|---|---|---|---|---|---|
| Agona | 36 | ± | ± | ± | ± | ± | ± |
| Agona | 75 | ± | ± | ± | ± | ± | ± |
| Agona | 117 | ± | ± | ± | ± | ± | ± |
| Agona | 121 | ± | ± | ± | ± | ± | ± |
| Enteritidis | 235 | ± | ± | ± | ± | ± | ± |
| Enteritidis | 236 | ± | ± | + | ± | ± | ± |
| Enteritidis | 237 | ± | ± | ± | ± | ± | ± |
| Enteritidis | 238 | ± | ± | ± | ± | ± | ± |
| Enteritidis | 239 | ± | ± | ± | ± | ± | ± |
| Enteritidis | 240 | ± | ± | ± | ± | ± | ± |
| Enteritidis | 241 | ± | ± | ± | ± | ± | ± |
| Enteritidis | 243 | ± | ± | − | ± | ± | ± |
| Enteritidis | 244 | ± | ± | ± | ± | ± | ± |
| Enteritidis | 246 | ± | ± | ± | ± | ± | ± |
| Enteritidis | 247 | ± | ± | ± | ± | ± | ± |
| Enteritidis | 248 | ± | ± | ± | ± | ± | ± |
| Enteritidis | 249 | ± | ± | ± | ± | ± | ± |
| Enteritidis | 250 | ± | ± | ± | ± | ± | ± |
| Enteritidis | 251 | ± | ± | ± | ± | ± | ± |
| Enteritidis | 252 | ± | ± | ± | ± | ± | ± |
| Enteritidis | 253 | ± | ± | ± | ± | ± | ± |
| Enteritidis | 255 | ± | ± | ± | ± | ± | ± |
| Enteritidis | 256 | ± | ± | ± | ± | ± | ± |
| Enteritidis | 261 | − | ± | − | ± | ± | ± |
| Enteritidis | 265 | ± | ± | ± | ± | ± | ± |
| Enteritidis | 266 | ± | ± | ± | ± | ± | ± |
| Enteritidis | 269 | ± | ± | ± | ± | ± | ± |
| Enteritidis | 270 | ± | ± | ± | ± | ± | ± |
| Enteritidis | 271 | ± | ± | ± | ± | ± | ± |
| Enteritidis | 272 | ± | ± | ± | ± | ± | ± |
| Enteritidis | 273 | ± | ± | ± | ± | ± | ± |
| Enteritidis | 274 | ± | ± | ± | ± | ± | ± |
| Enteritidis | 280 | ± | ± | ± | ± | ± | ± |
| Enteritidis | 281 | ± | ± | ± | ± | ± | ± |
| Enteritidis | 282 | ± | ± | ± | ± | ± | ± |
| Enteritidis | 320 | − | + | − | ± | ± | ± |
| Enteritidis | 322 | ± | ± | ± | ± | ± | ± |
| Enteritidis | 323 | ± | ± | ± | ± | ± | ± |
| Enteritidis | 324 | ± | ± | ± | ± | ± | ± |
| Enteritidis | 325 | ± | ± | ± | ± | ± | ± |
| Enteritidis | 327 | ± | ± | ± | ± | ± | ± |
| Enteritidis | 329 | ± | ± | ± | ± | ± | ± |
| Enteritidis | 330 | ± | ± | ± | ± | ± | ± |
| Enteritidis | 339 | ± | ± | ± | ± | ± | ± |
| Enteritidis | 340 | ± | ± | ± | ± | ± | ± |
| Enteritidis | 342 | ± | ± | ± | ± | ± | ± |
| Enteritidis | 369 | ± | ± | ± | ± | ± | ± |
| Enteritidis | 370 | ± | ± | ± | ± | ± | ± |
| Enteritidis | 371 | ± | ± | ± | ± | ± | ± |
| Enteritidis | 378 | ± | ± | ± | ± | ± | + |
| Enteritidis | 404 | + | + | + | + | + | + |
| Enteritidis | 407 | ± | ± | ± | ± | ± | ± |
| Enteritidis | 408 | ± | ± | ± | ± | ± | ± |
| Enteritidis | 457 | + | + | + | + | + | + |
| Enteritidis | 458 | + | + | + | + | + | + |
| Enteritidis | 460 | + | + | + | + | + | + |
| Enteritidis | 461 | + | + | + | + | + | + |
| Enteritidis | 463 | + | + | + | + | + | + |
| Enteritidis | 467 | + | − | ± | ± | ± | ± |
| Enteritidis | 469 | + | ± | ± | ± | ± | ± |
| Enteritidis | 475 | + | + | + | + | + | + |
| Enteritidis | 477 | + | + | + | + | + | + |
| Enteritidis | 478 | + | + | + | + | + | + |
| Enteritidis | 482 | + | + | + | + | + | + |
| Enteritidis | 483 | + | + | + | + | + | + |
| Enteritidis | 484 | + | + | + | + | + | + |
| Enteritidis | 488 | + | + | + | + | + | + |
| Enteritidis | 490 | + | + | + | + | + | + |
| Enteritidis | 493 | + | + | + | + | + | + |
| Enteritidis | 495 | + | + | + | + | + | + |
| Enteritidis | 496 | + | + | + | + | + | + |
| Hadar | 118 | − | ± | − | ± | ± | ± |
| Hadar | 119 | ± | − | − | ± | ± | ± |
| Hadar | 120 | − | − | − | − | − | − |
| Hadar | 122 | ± | − | − | ± | ± | − |
| Hadar | 124 | ± | − | − | ± | ± | ± |
| Hadar | 125 | ± | ± | ± | + | ± | ± |
| Hadar | 126 | + | − | − | + | + | + |
| Hadar | 127 | ± | ± | ± | ± | ± | − |
| Hadar | 128 | ± | ± | ± | ± | ± | ± |
| Hadar | 130 | ± | ± | − | ± | ± | − |
| Hadar | 131 | ± | − | − | ± | ± | ± |
| Hadar | 132 | ± | − | − | ± | ± | ± |
| Hadar | 133 | ± | − | ± | ± | ± | ± |
| Hadar | 134 | ± | − | − | ± | ± | − |
| Hadar | 135 | ± | ± | ± | + | ± | ± |
| Hadar | 136 | ± | ± | − | ± | ± | − |
| Hadar | 137 | ± | ± | − | ± | ± | − |
| Hadar | 138 | ± | ± | − | ± | ± | − |
| Hadar | 139 | ± | − | − | ± | ± | ± |
| Hadar | 163 | ± | − | − | ± | ± | ± |
| Hadar | 164 | ± | − | − | ± | ± | ± |
| Hadar | 165 | ± | − | − | ± | ± | ± |
| Hadar | 166 | ± | − | − | ± | + | + |
| Hadar | 167 | ± | − | − | ± | ± | ± |
| Hadar | 168 | ± | − | − | ± | ± | ± |
| Hadar | 169 | ± | − | − | ± | ± | ± |
| Hadar | 170 | ± | − | − | ± | ± | ± |
| Hadar | 171 | ± | − | − | ± | ± | ± |
| Hadar | 172 | ± | − | − | ± | ± | ± |
| Hadar | 173 | ± | − | − | ± | ± | ± |
| Hadar | 174 | + | − | − | − | ± | ± |
| Hadar | 178 | ± | ± | ± | ± | ± | ± |
| Heidelberg | 9 | + | ± | + | + | ± | + |
| Heidelberg | 14 | + | + | + | + | + | + |
| Heidelberg | 57 | + | ± | + | + | ± | + |
| Heidelberg | 260 | + | ± | + | + | ± | + |
| Heidelberg | 349 | + | ± | + | + | ± | + |
| Heidelberg | 350 | + | + | + | + | + | + |
| Heidelberg | 351 | + | ± | + | + | ± | + |
| Heidelberg | 352 | + | ± | + | + | ± | + |
| Heidelberg | 353 | + | ± | + | + | ± | + |
| Heidelberg | 354 | + | ± | + | + | ± | + |
| Heidelberg | 355 | + | ± | ± | + | ± | ± |
| Heidelberg | 356 | + | ± | + | + | ± | + |
| Heidelberg | 357 | + | ± | + | + | ± | + |
| Heidelberg | 358 | + | ± | + | + | ± | + |
| Heidelberg | 394 | + | ± | + | + | ± | + |
| Heidelberg | 395 | + | ± | ± | + | ± | ± |
| Heidelberg | 396 | + | ± | ± | ± | ± | ± |
| Heidelberg | 397 | + | ± | ± | ± | ± | ± |
| Heidelberg | 398 | + | + | + | + | + | + |
| Kentucky | 38 | ± | + | ± | + | + | ± |
| Kentucky | 39 | − | + | ± | + | + | ± |
| Kentucky | 66 | + | + | + | + | + | + |
| Kentucky | 103 | − | − | − | + | + | ± |
| Kentucky | 105 | − | + | − | + | + | − |
| Kentucky | 442 | − | ± | ± | + | + | ± |
| Newport | 245 | + | + | + | + | + | + |
| Newport | 267 | ± | + | − | ± | − | − |
| Newport | 268 | − | ± | − | − | − | − |
| Newport | 379 | + | ± | ± | + | + | ± |
| Newport | 380 | − | + | − | ± | ± | − |
| Newport | 381 | + | + | + | + | + | + |
| Newport | 382 | ± | + | ± | + | ± | ± |
| Newport | 383 | + | ± | − | − | − | − |
| Newport | 384 | + | + | + | + | + | + |
| Newport | 385 | + | ± | − | ± | − | − |
| Newport | 386 | ± | + | ± | + | ± | ± |
| Newport | 387 | + | ± | ± | + | ± | ± |
| Newport | 388 | + | + | + | + | + | + |
| Newport | 389 | + | ± | − | ± | ± | ± |

TABLE 2-continued

Lytic specificity of *Salmonella* bacteriophage for various *Salmonella* isolates.

| Serotype | Strain# | SPT-1 | SSE-121 | SIT-128 | SBA-178 | SBA-1781 | φSDT-15 |
|---|---|---|---|---|---|---|---|
| Newport | 390 | + | + | + | + | + | + |
| Newport | 391 | + | + | + | + | + | + |
| Newport | 392 | + | + | + | + | + | + |
| Newport | 393 | + | + | + | + | + | + |
| Typhimurium | 5 | ± | ± | ± | ± | ± | ± |
| Typhimurium | 187 | ± | ± | ± | ± | ± | ± |
| Typhimurium | 188 | ± | ± | ± | ± | ± | ± |
| Typhimurium | 189 | ± | ± | ± | ± | ± | ± |
| Typhimurium | 190 | ± | ± | ± | ± | ± | ± |
| Typhimurium | 191 | ± | ± | ± | ± | ± | ± |
| Typhimurium | 192 | ± | ± | ± | ± | ± | ± |
| Typhimurium | 193 | ± | ± | ± | ± | ± | ± |
| Typhimurium | 194 | ± | ± | ± | ± | ± | ± |
| Typhimurium | 195 | ± | ± | ± | ± | ± | ± |
| Typhimurium | 196 | ± | ± | ± | ± | ± | ± |
| Typhimurium | 197 | ± | ± | ± | ± | ± | ± |
| Typhimurium | 198 | − | ± | − | − | − | − |
| Typhimurium | 199 | ± | ± | ± | ± | ± | ± |
| Typhimurium | 200 | ± | ± | ± | ± | ± | ± |
| Typhimurium | 201 | ± | ± | ± | ± | ± | ± |
| Typhimurium | 202 | ± | ± | ± | ± | ± | ± |
| Typhimurium | 203 | ± | ± | ± | ± | ± | ± |
| Typhimurium | 204 | ± | ± | ± | ± | ± | ± |
| Typhimurium | 205 | ± | ± | + | ± | ± | + |
| Typhimurium | 206 | + | ± | ± | ± | ± | ± |
| Typhimurium | 207 | ± | ± | ± | ± | ± | ± |
| Typhimurium | 208 | ± | ± | ± | ± | ± | ± |
| Typhimurium | 209 | ± | ± | ± | ± | ± | ± |
| Typhimurium | 210 | − | − | − | ± | ± | − |
| Typhimurium | 211 | ± | ± | ± | ± | ± | ± |
| Typhimurium | 212 | ± | ± | ± | ± | ± | ± |
| Typhimurium | 213 | ± | ± | ± | ± | ± | ± |
| Typhimurium | 214 | ± | ± | ± | ± | ± | ± |
| Typhimurium | 215 | ± | ± | ± | ± | ± | ± |
| Typhimurium | 216 | ± | ± | ± | ± | ± | ± |
| Typhimurium | 217 | ± | ± | ± | ± | ± | ± |
| Typhimurium | 218 | ± | ± | ± | ± | ± | ± |
| Typhimurium | 219 | ± | ± | ± | ± | ± | ± |
| Typhimurium | 220 | ± | ± | ± | ± | ± | ± |
| Typhimurium | 221 | ± | ± | ± | ± | ± | ± |
| Typhimurium | 222 | ± | ± | ± | ± | ± | ± |
| Typhimurium | 223 | ± | ± | ± | ± | ± | ± |
| Typhimurium | 224 | + | + | + | + | + | + |
| Typhimurium | 225 | ± | ± | ± | ± | ± | ± |
| Typhimurium | 226 | − | ± | ± | ± | ± | − |

What is claimed is:

1. A substantially pure bacteriophage composition comprising at least one isolated *Salmonella* bacteriophage, deposited under ATCC Accession No. PTA-5280; PTA-5281; PTA-5282; PTA-5283; PTA-5284; or PTA-5285.

2. An isolated bacteriophage selected from the group consisting of SPT-1, SBA-178, SBA-1781, SIT-128, SSE-121, and SDT-15 deposited under ATCC Accession Nos. PTA-5281; PTA-5284; PTA-5282; PTA-5285; PTA-5283; or PTA-5280, respectively, and variants thereof, wherein said variants have the same phenotypic characteristics of said bacteriophage, and wherein said bacteriophage and variants thereof have the same lytic activity against *Salmonella* strains.

3. A composition comprising at least one of said bacteriophages of claim 2.

4. A composition comprising at least two of said bacteriophages of claim 2.

5. A composition comprising at least three of said bacteriophages of claim 2.

6. A composition comprising at least four of said bacteriophages of claim 2.

7. A composition comprising at least five of said bacteriophages of claim 2.

8. A composition comprising at least six of said bacteriophages of claim 2.

\* \* \* \* \*